US007026306B2

(12) United States Patent
Prokai et al.

(10) Patent No.: US 7,026,306 B2
(45) Date of Patent: *Apr. 11, 2006

(54) STEROIDAL QUINOLS AND THEIR USE FOR ANTIOXIDANT THERAPY

(75) Inventors: Laszlo Prokai, Gainesville, FL (US); Katalin Prokai, Gainesville, FL (US); James Simpkins, Fort Worth, TX (US)

(73) Assignees: University of Florida Research Foundation, Inc., Gainesville, FL (US); University of North Texas Health Science Center, Forth Worth, TX (US)

( * ) Notice: Subject to any disclaimer, the term of this patent is extended or adjusted under 35 U.S.C. 154(b) by 331 days.

This patent is subject to a terminal disclaimer.

(21) Appl. No.: 10/405,413

(22) Filed: Apr. 1, 2003

(65) Prior Publication Data

US 2003/0229060 A1 Dec. 11, 2003

Related U.S. Application Data

(60) Provisional application No. 60/369,589, filed on Apr. 1, 2002.

(51) Int. Cl.
*A61K 31/56* (2006.01)
*C07J 1/00* (2006.01)

(52) U.S. Cl. ...................... 514/178; 552/612
(58) Field of Classification Search ............... 514/178; 552/612
See application file for complete search history.

(56) References Cited

U.S. PATENT DOCUMENTS

| 2,910,486 | A | * | 10/1959 | Jiu ............................. 552/612 |
| 2,950,291 | A | * | 8/1960 | Jin ............................. 552/613 |
| 5,108,996 | A | | 4/1992 | Claussner et al. |
| 5,395,831 | A | | 3/1995 | Gemmill, Jr. et al. |
| 5,552,395 | A | | 9/1996 | Gemmill, Jr. et al. |
| 5,554,601 | A | | 9/1996 | Simpkins et al. |
| 5,859,001 | A | | 1/1999 | Simpkins et al. |
| 5,891,878 | A | | 4/1999 | Beasley et al. |
| 6,197,833 | B1 | | 3/2001 | Simpkins et al. |
| 6,319,914 | B1 | | 11/2001 | Simpkins et al. |
| 2003/0050295 | A1 | | 3/2003 | Pang |
| 2003/0105167 | A1 | | 6/2003 | Dykens |
| 2004/0214806 | A1 | | 10/2004 | Pang |

FOREIGN PATENT DOCUMENTS

WO    WO 03/084978 A    10/2003

OTHER PUBLICATIONS

Numazawa et al., Chem. Pharm. Bull., vol. 37(8), pp. 2058-2062, 1989.*
Breuer, H. and Koster, G "Interaction Between Oestrogens and Neurotransmitters at the Hypophysial-Hypothalamic Level" *Journal of Steroid Biochemistry*, 1974, pp. 961-967, vol. 5.
Hiemke, C. et al. "Actions of Sex Hormones on the Brain" *Prog. Neuro-Psychopharmacol & Biol.Psychiat*, 1992, pp. 377-388, vol. 16.
Liang, Y. et al. "Membrane Fluidity Effects of Estratrienes" *Brain Research Bulletin*, 2001, pp. 661-668, vol. 54, No. 6.
Milic, D. et al. "X-Ray Crystal Structure of 10β-Hydroxy-4β,5β-expoxyerstr-1-ene-3,17-dione and Antitumor Activity of its Congeners" *Molecules*, 1999, pp. 338-352, vol. 4.
Milic, D. et al. "The Synthesis and Biological Evaluation of A-Ring Substituted Steroidal p-Quinones" *Tetrahedron*, 1997, pp. 14073-14084, vol. 53, No. 41.
Milic, D. et al. "Structure and Reactivity of Steroidal Quinones" *J. Serb. Chem. Soc.*, 1997, pp. 755-768, vol. 62, No. 9.
Ohe, T. et al. "Novel Metabolic Pathway of Estrone and 17β-Estradiol Catalyzed by Cytochrome P-450" *Drug Metabolism and Disposition*, 2000, pp. 110-112, vol. 28, No. 2.
Prokai, L. et al. "Synthesis and Biological Evaluation of 17β-Alkoxyestra-1,3,5(10)-trienes as Potential Neuroprotectants Against Oxidative Stress" *J. Med. Chem.*, 2001, pp. 110-114, vol. 44.
Solaja, B. et al. "A Novel m-CPBA Oxidation: p-Quinols and Epoxyquinols from Phenols" *Tetrahedron Letters*, 1996, pp. 3765-3768, vol. 37, No. 21.
Galdecki, Z., P. et al. (1987) "Structure of 2,4-Dibromo-10β, 17β-dihydroxy-1,4-estradien-3-one" *Acta Cryst.* vol. c43, pp. 967-968.
Kupfer, Rene, Long Yu Liu, Alban J. Allentoff, John A. Thompson (2001) "Comparisons of Hydroperoxide Isomerase and Monooxygenase Activities of Cytochrome P450 for Conversions of Allylic Hydroperoxides and Alcohols to Epoxyalcohols and Diols: Probing Substrate Reorientation in the Active Site" *Biochemistry* 40:11490-11501.
McCullough, Louise D. and Patricia D. Hurn (Jul. 2003) "Estrogen and Ischemic Neuroprotection: an integrated view" *Trends in Endocrinology and Metabolism* 14(5):228-235.
Nilsen, Jon and Roberta Diaz Brinton (Jan. 2002) "Impact of Progestins on Estrogen-Induced Neuroprotection: Synergy by Progesterone and 19-Norprogesterone and Antagonism by Medroxyprogesterone Acetate" *Endocrinology* 143(1): 205-212.

(Continued)

*Primary Examiner*—Barbara P. Badio
(74) *Attorney, Agent, or Firm*—Saliwanchik, Lloyd & Saliwanchik (57) ABSTRACT

The present invention relates to novel estrogen-related steroidal quinols and their use as prodrugs for phenolic estrogens and estrogen analogs. The quinols of the present invention provide improved physicochemical properties, increased bioavailability, and improved distribution into tissues and penetration across the blood-brain barrier when compared to phenolic estrogens and estrogen analogs.

8 Claims, 8 Drawing Sheets

OTHER PUBLICATIONS

Numazawa, Mitsuteru, Kumiko Hoshi, Katsuhiko Kimura (1989) "Oxygenation of 2,4-Dibromoestrogens with Nitric Acid: A New Synthesis of 19-Nor Steroids" *Chem. Pharm Bull.* 37(8):2058-2062.

Ohe, Tomoyuki, Masaaki Hirobe, Tadahiko Mashino (2000) "Novel Metabolic Pathway of Estrone and 17β-Estradiol Catalyzed by Cytochrome P-450" *Drug Metabolism and Disposition* 28(2):110-112.

Nilsen, Jon and Roberta Diaz Brinton (Sep. 2, 2003) "Divergent impact of progesterone and medroxyprogestoner acetate (Provera) on nuclear mitogen-activated protein kinase signaling" *PNAS* vol. 100, No. 18, pp. 10506-10511.

Prokai Laszlo, et al. (Sep. 30, 2003) "Quninol-based cyclic antioxidant mechanism in estrogen neuroprotein" *PNAS* vol. 100, No. 20, pp. 11741-11746.

Prokai, Laszlo, et al. (2003) "Short Communication: Quinol-based Metabolic Cycle for Estrogen in Rat Liver Microsomes" *Drug Metabolism and Disposition* vol. 31, No. 6, pp. 701-704.

Prokai-Tatrai, Katalin and Laszlo Prokai (2003) "Modifying peptide properties by prodrug design for enhanced transport into the CNS" *Progress in Drug Research*. vol. 61, pp. 155-188.

Prokai, Laszlo, Katalin Prokai-Tatrai, and Nicholas Bodor (2000) "Targeting Drugs to the Brain by Redox Chemical Delivery Systems" *Med Res Rev*, vol. 20, No. 5, pp. 367-416.

Beers, M.H. and R. Berkow, Editors, The Merck Manual of diagnosis and therapy, pp. 471-473 and pp. 1942-1944 (1999) Merck Research Laboratories, Whitehouse Station, N.J. USA.

Lupon, P. et al. (1983) "Photooxygenierung von Oestrogenen: Eine Neu 19-Norsteroid-Synthese" Verlagsgesellschaft, Weinheim, DE, vol. 95, No. 9, p. 757.

Sedee, A.G. J. et al. (1983) "A sintesis for p-quinol compounds from phenols fused with other saturated rings" *Tetrahedron Letters* 24(51):5779-5780.

* cited by examiner

STEROIDAL QUINOLS AND THEIR USE FOR ANTIOXIDANT THERAPY

CROSS-REFERENCE TO RELATED APPLICATIONS

This application claims the benefit of U.S. Provisional application No. 60/369,589, filed Apr. 1, 2002.

GOVERNMENT SUPPORT

This invention was made with government support under a grant awarded from the National Institute of Neurological Disorders and Stroke under grant number NS44765 and a grant from the National Institutes of Health on Aging under grant number PO1 AG10485. The government has certain rights in the invention.

BACKGROUND OF THE INVENTION

The present invention relates to prodrugs for antioxidant therapy. In particular, the present invention relates to estrogen-related steroidal quinols and their use as prodrugs for phenolic A-ring estrogens and estrogen analogs.

Mammalian cells are continuously exposed to reactive oxygen species (ROS) such as lipid peroxyl, oxoperoxinitrate, superoxide ($O_2.^-$), hydrogen peroxide ($H_2O_2$), hydroxyl radical (OH.), and singlet oxygen ($^1O_2$). In vivo, these reactive oxygen intermediates are generated by cells in response to aerobic metabolism, catabolism of drugs and other xenobiotics, ultraviolet and x-ray radiation, and the respiratory burst of phagocytic cells (such as white blood cells) to kill invading bacteria such as those introduced through wounds. Hydrogen peroxide, for example, is produced during respiration of most living organisms especially by stressed and injured cells.

ROS, when present in excess, can be detrimental to cells. If the cellular balance of the level of oxidizing species (i.e., reactive oxygen species and reactive nitrogen species) is not restored, several pathological processes are elicited, including DNA damage, lipid peroxidation, loss of intracellular calcium homeostasis, and alteration in cellular signaling and metabolic pathways. Oxidative stress causes cellular damage, resulting in alteration of the redox state (i.e., depletion of nucleotide coenzymes and disturbance of sulfhydryl-containing enzymes), and saturation and destruction of the antioxidant defense and DNA repair system.

For example, excess hydrogen peroxide can react with DNA to cause backbone breakage, produce mutations, and alter and liberate bases. Such oxidative biochemical injury can result in the loss of cellular membrane integrity, reduced enzyme activity, changes in transport kinetics, changes in membrane lipid content, and leakage of potassium ions, amino acids, and other cellular material.

Another example of the ability of ROS to injure cells is lipid peroxidation, which involves the oxidative degradation of unsaturated lipids. Lipid peroxidation is highly injurious to membrane structure and function and can cause numerous cytopathological effects. Researchers propose that atherosclerosis and its deadly effects of heart attack and stroke develop in relationship to the oxidation modification of low-density lipoproteins (LDL) carrying cholesterol in the blood. It is theorized that free radicals generated by the body's own immune cells oxidize LDL, which are taken up by cells of the vascular intima initiating the atherosclerosis lesion.

Thus, oxidative stress has been associated with a variety of diseases and disorders, including aging and neuronal cell death (Jenner, P., "Oxidative damage in neurodegenerative disease," *Lancet,* 344, 796–798 (1994)). For example, oxidative stress is associated with the pathology of numerous neurodegenerative diseases and conditions including, but not limited to, Alzheimer's disease, diabetic peripheral neuropathy, multiple sclerosis, amyotrophic lateral sclerosis, Huntington's disease, and Parkinson's disease.

The brain is a specialized organ that concentrates metals necessary for normal neurological functions. However, trauma, ischemia, and many other insults of neuropathological origin are known to release protein bound metal ions such as iron from damaged cells. The release of metal ions increases oxidative stress in the central nervous system (CNS) by promoting the generation of ROS.

Antioxidants have been shown to inhibit damage associated with ROS. For example, pyruvate and other alpha-ketoacids have been reported to react rapidly and stoichiometrically with hydrogen peroxide to protect cells from cytolytic effects (O'Donnell-Tormey et al., "Secretion of pyruvate. An antioxidant defense of mammalian cells," *J Exp. Med.,* 165, 500–514 (1987)). Selegiline, which may act as an antioxidant since it inhibits oxidative deamination, has been found to delay the onset of Parkinson's disease (Youdim, M. B. H., and Riederer, P., "Understanding Parkinson's disease," *Scientific American* January, 52–59 (1997)). Antioxidant therapy has been demonstrated to slow the rate of motor decline early in the course of Huntington's disease (Peyser C. E., et al., "Trial of d-alpha-tocopherol in Huntington's disease," *Am J. Psychiatry,* 152, 1771–1775 (1995)). PROBUCOL (4,4'-[(1-methylethylidene)bis(thio)] bis[2, 6-bis(1,1-dimethylethyl)] (Lorelco, Marion Merrell Dow), an antioxidant, is effective in reducing the rate of restenosis after balloon coronary angioplasty (Tardif, J. C. et al., "Probucol and multivitamins in the prevention of restenosis after coronary angioplasty. Multivitamins and Probucol Study Group," *New Engl. J. Med.* 337, 365–372 (1997)).

Unfortunately, many antioxidants are fat-soluble and restricted in usage because of low water solubility. Those antioxidants that are water-soluble and less restricted in usage, such as vitamin C, may act as a pro-oxidant, i.e. an oxidation promoter in the presence of a metallic ion, and have the drawback of promoting lipid peroxidation under certain conditions. Uric acid is also water-soluble, but when accumulated in vivo, may generate unpleasant side effects such as gout or renal calculus. PROBUCOL demonstrates little bioavailability.

Estrogens have been recognized as antioxidants and potent neuroprotective agents. Their antioxidant action is believed to be due to their ability to scavenge free radicals that cause neuronal cell death. Estrogens, like the highly potent endogenous antioxidant vitamin E (α-Tocopherol), have a phenolic moiety considered a quintessential feature in achieving protection against oxidative stress. Studies, however, have concluded that the potency of the estrogen estradiol as a phenolic antioxidant on inhibiting iron-induced lipid peroxidation to be greater than that of vitamin E despite the extremely low overall concentration of estrogens compared to vitamin E. In addition, the OH- bond dissociation energy (BDE) of estradiol is greater than that of vitamin E, which would imply that vitamin E is a stronger deactivator of oxyradicals than estrogen. Antioxidant potency is generally determined not only by the chemical reactivity toward ROS, but also by the mobility and/or distribution of the molecule in the microenvironment and the fate of the antioxidant derived radicals (i.e., the dynamics of antioxidant action). Therefore, lipophilic estrogens may act in vivo as highly localized antioxidants despite their small bulk levels due to membrane binding affinity and high concentrations near the loci of activity.

Estrogen replacement therapy (ERT) has been associated with numerous health benefits, including alleviation of menopausal symptoms, bone and cardiovascular protection, reduction in the incidence of Alzheimer's disease, and improvement in cognitive functions, Parkinson's disease, and the outcome of stroke. These diverse activities of estrogens may be related to their cytoprotective effects and antioxidant abilities. The neuroprotective effect of estrogens against numerous toxic insults including oxidative stress has been extensively investigated in vivo and in vitro in several types of neuronal cells. There is mounting evidence that estrogens exert their neuroprotective effect against oxidative stress by suppressing the neurotoxic stimuli via their direct radical-scavenging activity.

Estrogens are degraded in the intestinal tract and rapidly metabolized by the liver. Specifically, estrogens undergo enterohepatic recirculation via sulfate and glucuronide conjugation in the liver, biliary secretion of conjugates into the intestine, and hydrolysis in the gut followed by reabsorption. The estrogen concentration encountered by the liver is generally four-fold to five-fold greater than estrogen levels in peripheral blood (the "first pass effect"). Administration of oral estrogens present high levels to the liver and may lead to an undesirable increase in the production of certain coagulation factors and renin substrates by the liver. Therefore, there is a need for therapeutic agents that are pharmaceutically effective at those regions where they are required.

High doses of estrogen have been demonstrated as having achieved an anti-oxidant effect in vitro. It has been demonstrated that the most biologically active estrogen, 17β-estradiol, is a potent antioxidant and has neuroprotective activity; however, the mechanism of action is still unclear. Such doses, even if effective on cells in vivo, would have limited utility in treating conditions associated with oxidative stress because of associated problems with toxicity, increased incidence of some forms of cancer, and feminizing effects on men. Thus, the usefulness of such a method of treatment is quite limited.

Therefore, a need exists for compositions and methods of administering estrogen-related free-radical scavengers or antioxidants to tissues demonstrating alterations in oxidative conditions. In particular, there is a need for compositions and methods that can provide therapeutic benefits to subjects suffering from neurodegenerative diseases associated with oxidative stress. Furthermore, there exists a need for a therapeutically effective estrogen compound that retains its therapeutic activity without any associated sex-related side effects.

BRIEF SUMMARY OF THE INVENTION

The present invention provides compositions and methods for the controlled administration of antioxidant compounds to mammals. In a preferred embodiment, the present invention provides estrogen-related steroidal quinols and their use as prodrugs for antioxidant therapy to treat and/or prevent various disorders and diseases associated with free radicals and oxidative damage.

In one aspect of the subject invention, estrogen-related steroidal quinols are administered to treat neurological diseases involving oxidative stress, such as Alzheimer's disease or Parkinson's disease. In further aspects of the invention, estrogen-related steroidal quinols are administered to mitigate the adverse effects associated with aging, stroke, and trauma.

In a preferred embodiment, the present invention provides inactive compounds that are converted in vivo into biologically active, therapeutic compounds by chemical or enzymatic transformation. The steroid-related quinols of the present invention are advantageous because they overcome problems associated with stability, toxicity, lack of specificity, and limited bioavailability, which may exist with the active form of the steroid. The quinols according to the present invention are particularly advantageous as oxidative scavengers.

The subject invention exploits the identification of a mechanism by which estrogens serve as potent scavengers of hydroxyl radicals through the capture of harmful reactive oxygen species. Specifically, in a preferred embodiment, the present invention provides an estrogen-related quinol that is rapidly converted to a biologically active estrogen compound via enzyme-catalyzed reduction that utilizes an endogenous reducing agent. The endogenous reducing agent may be, for example, the reduced forms of nicotinamide adenine dinucleotide (NADH) or nicotinamide adenine dinucleotide phosphate (NADPH). An advantage of the chemical conversion reaction is that the ensuing redox cycle does not generate reactive oxygen species.

In a specific embodiment the present invention provides estrogen-related steroidal quinols that are related to a 10 β-hydroxyestra-1,4-diene-3-one structure. Such quinols are advantageous because they can be converted in vivo into a parent phenolic A-ring estrogen, or estrogen analog compound, upon exposure to a reducing agent including, for example, endogenous NADPH.

Advantageously, capturing a free-radical after in vivo reduction to the active parent phenolic structure regenerates the estrogen-related steroidal quinols of the subject invention. This is advantageous because other prodrugs are usually not regenerated after their in vivo activation. In having the ability to regenerate, the beneficial therapeutic effects of the quinols are prolonged.

The present invention also concerns quinols having improved physiochemical properties when compared to lipophilic phenols such as estrogens and estrogen analogs. Advantageously, quinols of the invention demonstrate decreased lipophilicity. For preferred compounds of the subject invention there is a 10-fold to 50-fold decrease in the n-octanol/water partition coefficient (P) equivalent with ΔlogP of 1.0 to 1.7.

In addition, the present invention provides quinols having improved distribution into the central nervous system (CNS) as compared to lipophilic phenols such as estrogens and estrogen analogs. Further, the quinols of the invention demonstrate enhanced penetration across the blood-brain barrier.

The present invention also pertains to pharmaceutical compositions that comprise a therapeutically effective amount of one or more steroid-related quinols in pharmaceutical dosage form to treat and/or prevent diseases and disorders associated with oxidative stress. Using the steroid-related quinols results in the reduction of peaks and troughs characteristic of dosing with a pharmaceutically active parent agent. Improved dose administrations result in the reduction of toxicity compared to the administration of active estrogen compounds. In addition, pharmaceutical compositions of the present invention have an increased therapeutic index compared to the active parent steroid.

In another aspect, the present invention concerns therapeutic methods for the controlled administration to a mammal of an effective amount of at least one or more of the steroid-related quinols described herein to provide antioxidant therapy.

DETAILED DISCLOSURE OF THE INVENTION

In accordance with the present invention, certain estrogen-related steroidal quinol compounds are administered for the treatment and/or prevention of pathological conditions associated with reactive oxygen species (ROS). The methods and compositions of the subject invention take advantage of the identification of a mechanism by which estrogens serve as potent hydroxyl scavengers. Due to the ability of the present compounds to be converted into active estrogen-related steroidal compounds via enzyme-catalyzed reduction, their administration as prodrugs is quite advantageous.

Advantageously, the present invention provides prodrug forms of estrogen and estrogen analogs which provide prolonged beneficial pharmaceutical effects, improved physicochemical properties, improved tissue distribution, increased bioavailability, resistance to metabolic inactivation, and reduced toxicity, in comparison to lipophilic, phenolic estrogens and estrogen analogs. Prodrug compounds according to the present invention are unique and advantageous radical scavengers due to their ability to regenerate after in vivo reductive activation into an active steroidal phenol structure.

In contrast with the catechol structure of the well-known phenolic estrogen products, the subject steroidal quinols confer a non-aromatic nature to the steroidal A-ring. Thus, the biochemistry of the steroidal quinols according to the subject invention is substantially different from that of catechol estrogens to provide improved beneficial properties. In a particular embodiment, the estrogen-related steroidal quinols are non-aromatic until introduction to a chemical or enzymatic reductive aromatization process to provide a phenolic moiety and neuroprotection. Thus, the steroidal quinol compound serves as a prodrug for active neuroprotective estrogens.

In a preferred embodiment, the present invention provides estrogen-related steroidal quinol compounds of the formula:

wherein
R is H, alkyl, cycloalkyl, aryl, heterocycle, heteroaryl, alkylamino, hydroxyalkyl, alkoxyalkyl or alkylaryl;

X is hydrogen, halogen, isopropyl, alkyl, alkenyl, alkynyl, carbocycle, cycloalkyl, aryl, heterocycle, heteroaryl, alkylamino, hydroxyalkyl, alkoxyalkyl, or a linear or branched hydrocarbon from 1–15 atoms carbon atoms in length, that can optionally include one or more heteroatoms in the chain;

Y is hydrogen, halogen, isopropyl, alkyl, alkenyl, alkynyl, carbocycle, cycloalkyl, aryl, heterocycle, heteroaryl, alkylamino, hydroxyalkyl, alkoxyalkyl, or a linear or branched hydrocarbon from 1–15 atoms carbon atoms in length, that can optionally include one or more heteroatoms in the chain; and Z is hydrogen, halogen, isopropyl, alkyl, alkenyl, alkynyl, carbocycle, cycloalkyl, aryl, heterocycle, heteroaryl, alkylamino, hydroxyalkyl, alkoxyalkyl, or a linear or branched hydrocarbon from 1–15 atoms carbon atoms in length, that can optionally include one or more heteroatoms in the chain.

In one embodiment, R is a straight or branched $C_{1-20}$ alkyl chain and X, Y, and Z are hydrogen. In another embodiment, X is hydrogen. In another embodiment, X and Y are hydrogen. In yet another embodiment, X and Z are hydrogen.

The term "estrogen compound," as used herein, refers to estrogen; estrogen metabolites; estrogen analogs, antagonists, or modulators; and compounds with attributes that are categorized as similar or analogous to estrogen, estrogen metabolites, or estrogen analogs, antagonists, or modulators.

The term "patient," as used herein, describes an animal, including mammals, to which treatment with the compositions according to the present invention is provided. Mammalian species that benefit from the disclosed methods of treatment include, and are not limited to, apes, chimpanzees, orangutans, humans, monkeys; and domesticated animals (e.g., pets) such as dogs, cats, guinea pigs, and hamsters.

As used herein, the term "prodrug" denotes a molecule that is incapable of exerting the pharmacological activity of the active compound. The active compound will exert its therapeutic effects after it is bioactivated by a reducing agent.

Figure 1:
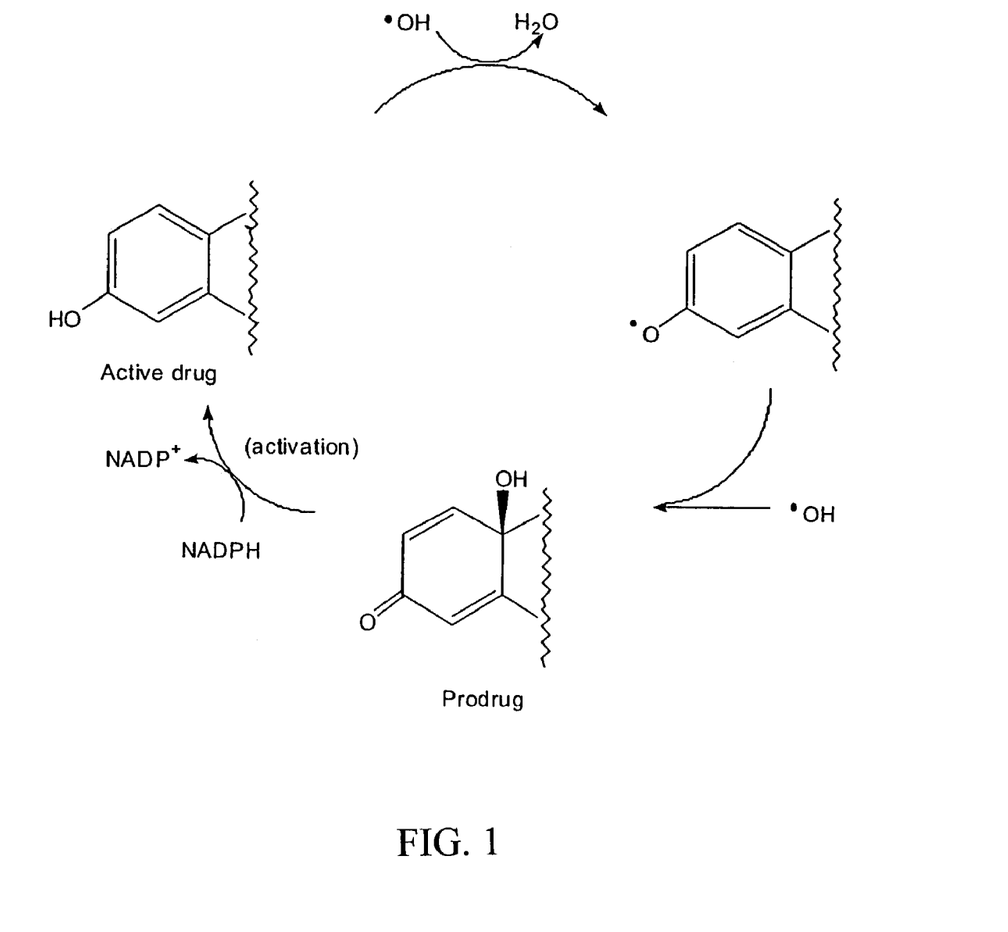
FIG. 1 illustrates the activation mechanism of the estrogen-related steroidal quinols of the present invention.

A variety of endogenous reducing agents are known and may be used to achieve preferential bioactivation of the active compound within the body. Candidate reducing agents that could be utilized to activate the prodrugs according to the present invention include NADH or NADPH. As a result of the bioactivation, the quinol prodrugs are converted to an active phenolic estrogen or estrogen analog. The estrogen-related steroidal quinols of the subject invention are advantageous as prodrugs because, once reduced to an active compound by a reducing agent, the active compound is readily reoxidized back into the estrogen-related steroidal quinol by an oxidant, such as a hydroxyl-radical. This process is shown in FIG. 1. Advantageously, the ability to regenerate the prodrug compounds of the invention after bioactivation facilitates the prolongation of beneficial pharmacological effects.

Compounds of the invention may be used with pharmaceutically acceptable carriers, additives, or excipients, the proportions of which are determined by the solubility and chemical nature of the compound, chosen route of administration, and standard medical practice. In one embodiment of the present invention, pharmaceutical compositions include a therapeutically effective amount of any one or more of the compounds of the invention in pharmaceutical dosage form to treat and/or prevent diseases and disorders associated with oxidative stress. The therapeutically effective amount will vary with the condition to be treated, its severity, the treatment regimen to be employed, the pharmacokinetics of the agent used, as well as the patient treated.

The prodrug compounds of the subject invention can be formulated according to known methods for preparing pharmaceutically useful compositions. Formulations are described in a number of sources, which are well known and readily available to those skilled in the art. For example, *Remington's Pharmaceutical Science* (Martin E W [1995] Easton Pa., Mack Publishing Company, 19$^{th}$ ed.) describes formulations that can be used in connection with the subject invention. Formulations suitable for parenteral administration include, for example, aqueous sterile injection solutions, which may contain antioxidants, buffers, bacteriostats, and solutes, which render the formulation isotonic with the blood of the intended recipient; and aqueous and nonaqueous sterile suspensions, which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question.

Tissues that are protected by the use of the estrogen-related steroidal quinol compounds as prodrugs may be from children, adult or fetuses and include, but are not limited to, stem cells, blood and all of its components, including erythrocytes, leukocytes, platelets and serum, central nervous tissue, including brain and spinal cord tissue, neurons, and glia; peripheral nervous tissue, including ganglia, posterior pituitary gland, adrenal medulla, and pineal; connective tissue, skin, ligaments, tendons, and fibroblasts; muscle tissue, including skeletal, smooth and cardiac tissues or the cells therefrom; endocrine tissue, including anterior pituitary gland, thyroid gland, parathyroid gland, adrenal cortex, pancreas and its subparts, testes, ovaries, placenta, and the endocrine cells that are a part of each of these tissues; blood vessels, including arteries, veins, capillaries and the cells from these vessels: lung tissue; heart tissue and whole organ; heart valves; liver; kidney; intestines; bone, including osteocytes, osteoblasts and osteoclasts; immune tissue, including blood cells, bone marrow and spleen; eyes and their parts; reproductive tract tissues; or urinary tract tissue.

Examples of degenerative diseases, disorders and conditions that can be treated with the estrogen-related steroidal quinol compounds of the subject invention include: neurological and neurodegenerative diseases and conditions such as Alzheimer's disease, Parkinson's disease, amyotrophic lateral sclerosis (ALS), multiple sclerosis, peripheral neuropathy, shingles, stroke, traumatic injury, and various neurological and other degenerative consequences of neurological and chest surgeries, schizophrenia, epilepsy, Down's Syndrome, and Turner's Syndrome; degenerative conditions associated with AIDS; various bone disorders including osteoporosis, osteomyclitis, ischemic bone disease, fibrous dysplasia, rickets, Cushing's syndrome and osteoarthritis; other types of arthritis and conditions of connective tissue and cartilage degeneration including rheumatoid, psoriatic and infectious arthritis; various infectious diseases; muscle wasting disorders such as muscular dystrophy; skin disorders such as dernatitis, eczema, psoriasis and skin aging; degenerative disorders of the eye including macular degeneration and retinal degeneration; disorders of the ear such as otosclerosis; impaired wound healing; various cardiovascular diseases and conditions including stroke, cardiac ischemia, myocardial infarction, chronic or acute heart failure, cardiac dysrhymias, artrial fibrillation, paroxysmal tachycardia, ventricular fibrillation and congestive heart failure; circulatory disorders including atherosclerosis, arterial sclerosis and peripheral vascular disease, diabetes (Type I or Type II); various diseases of the lung disorders and diseases including lung cancer, pneumonia, chronic obstructive lung disease (bronchitis, emphysemia, asthma); disorders of the gastrointestinal tract such as ulcers and hernia; dental conditions such as periodontitis; liver diseases including hepatitis and cirrhosis; pancreatic ailments including acute pancreatitis; kidney diseases such as acute renal failure and glomerulonepritis; and various blood disorders such as vascular amyloidosis, aneurysms, anemia, hemorrhage, sickle cell anemia, autoimmune disease, red blood cell fragmentation syndrome, neutropenia, leukopenia, bone marrow aphasia, pancytopenia, thrombocytopenia, and hemophilia. The preceding list of diseases and conditions which are treatable according to the subject invention is not intended to be exhaustive or limiting but presented as examples of such degenerative diseases and conditions.

Pharmaceutical compositions based upon these estrogen-related steroidal quinol compounds may be formulated for a variety of routes of administration, including, for example, orally-administrable forms such as tablets, capsules or the like, or via parenteral, intravenous, intramuscular, transdermal, buccal, subcutaneous, suppository, or other route. In certain pharmaceutical dosage forms, certain of the present compounds may be more appropriate than other compounds, depending upon the route of administration and the targeted site within the patient.

Therapeutic methods according to the present invention include the controlled administration to a patient of an effective amount of at least one or more of the compounds as set forth above to provide antioxidant therapy. Administration to a patient may range from continuous (intravenous drip) to intramuscular, to several oral administrations per day (for example, Q.I.D.) and may include parenteral, including intravenous and intramuscular, oral, topical, subcutaneous, transdermal (which may include a penetration agent), buccal and suppository administration, among other routes of administration.

To prepare the pharmaceutical compositions according to the present invention, a therapeutically effective amount of one or more of the compounds according to the present invention is preferably intimately admixed with an optional pharmaceutically acceptable carrier according to conventional pharmaceutical compounding techniques to produce a dose. A carrier may take a wide variety of forms depending on the form of preparation desired for administration, e.g., oral or parenteral.

For parenteral formulations, the carrier may comprise sterile water or aqueous sodium chloride solution in combination with other ingredients that aid dispersion, such as ethanol and other pharmaceutically acceptable solvents. Of course, where solutions are to be used and maintained as sterile, the compositions and carrier must also be sterilized. Injectable suspensions may also be prepared, in which case appropriate liquid carriers, suspending agents and the like may be employed.

In preparing pharmaceutical compositions in oral dosage form according to the present invention, any one or more of the usual pharmaceutical media may be used. Thus, for liquid oral preparations such as suspensions, elixirs and solutions, suitable carriers and additives including water, glycols, oils, alcohols, flavoring agents, preservatives, coloring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, tablets or capsules may be enteric-coated or sustained release by standard techniques.

The estrogen-related steroidal quinols of the present invention may be prepared using known reagents and reactions, including for example, oxidation of estradiol or estrone with tallium, trifluoroacetate, lead tetraacetate, para-nitroperoxybenzoic acid, photooxygenation, or the like. The following Examples 1–10 are exemplary and provided for purposes of illustration and are not intended to be limitative.

Examples 1–6 are preparatory schemes for prodrug compounds according to the present invention.

EXAMPLE 1

Synthesis of Estrone-Quinol By Transforming Phenol-to-Quinol

As understood by the skilled artisan, 10β-hydroxyestra-1,4-diene-3,17-dione (estrone-quinol) may be synthesized using a "one-pot" phenol-to-quinol transformation. The synthesis method utilizes meta-chloroperbenzoic acid (m-CPBA) as an oxidant, d[i]ebenzoyl peroxide [(PheCO)$_2$O$_2$] as a radical initiator and visible-light irradiation that, in refluxing aprotic solvent, produces excellent yields of the quinols of the present invention.

By way of example, Milic et al., Tetrahedron Letters, 37:21, 3765–3768 (1996) disclose a "one-pot" method for synthesizing estrone-quinol. Oxidation of estrone to synthesize 10β-hydroxyestra-1,4-diene-3,17-dione is performed by heating a stirred solution of estrone (10.00 g, 37.0 mmol), meta-chloroperoxybenzoic acid (m-CPBA) (22.53 g, 111.0 mmol; 85% Jansen Chimica), and (PheCO)$_2$O$_2$ (900 mg, 3.70 mmol) in 2 L mixture of CCl$_4$/Me$_2$CO (4/1) to reflux for 3 hours while irradiated with a 60 Watt tungsten lamp. Upon evaporation of the solvent, extraction is performed with CHCl$_3$ (3×200 mL), washing with NaHCO$_3$ (2×100 mL) and H$_2$O (100 mL), and drying over anhydrous Na$_2$SO$_4$. The residue is then chromatographed on SiO$_2$ column. Elution may be performed with PhMe/EtOAc (1/1 and 7/3, respectively) and crystallization from benzene produces 5.19 g (49%) of estrone quinol as colorless needles.

Data regarding the resulting estrone quinols, as observed by Milic et al. are as follows: mp=219–221° C. (benzene); Lit.[4]=215–217° C.; [α]24.0 546=+62, [α]24.0578 =+68 (c=1.32, chl.); UV:λMeOH max=229 nm (15500); IR(KBr): 3359x, 2941 m, 1736s, 1664s, 1622s, 1601m cm$^{-1}$; $^1$H NMR (250 MHz, DMSO-d$_6$): 7.13 (d,j=10.4 Hz, H-C(1)), 6.07 (dd, J=10.4, 2.4 Hz, H-C(2)), 5.92 (irreg. T, J$_{4,2}$=2.4, J$_{4,6β}$=1.2 Hz, H-C(4)), 5,67 (s, H-o, exchangeable with D$_2$O), 2.67 (tdd, J=15.2, 6.4, 1.2 Hz, H$_β$-C(6)), 1.97–1.83 (m, H$_β$-C(8) and H$_β$-C(11)—from NOE DIFF. Spectrum), 1.30–1.18 (m, H$_α$C(11)), 0.97 (s, H$_3$C—C(13)); $^{13}$C NMR (62.9 MHz, DMSO-d$_6$): 220.33 (C(17)), 185,53 (C(3)), 165.09 (C(5)), 150.25 (C(1)), 128.30 (C(2)), 123.09 (C(4)), 70.10 (C(10)), 51.18(C(()), 50.10 (C(14)), 47.75 (C(13)), 35.62 (C(16)), 34.58 (C(8)), 32.19 (C(7)), 31.80(C(6)), 31.03 (C(11)), 22.00 (C(12)), 21.90 (C(15)), 13.73 (C(18)); MS (EI, m/z): 286(M$^+$, 84), 268(M$^+$-H$_2$O, 39), 150(68), 145(100), 124(75), 107(50), 91(50), 79(54), 55(60); Anal. Calcd. for C$_{18}$H$_{22}$O$_3$ (286.37): C, 75.50; H. 7.74; Found: C =75.41, H=7.76.

Melting points were determined on a Boetius PMHD apparatus and were not corrected. Specific rotations were measured on a Perkin-Elmer 141 MC and Karl Zeiss Polamat A polarimeters at the given temperatures. IR spectra were recorded on Perkin-Elmer spectrophotometer FT-IR 1725x. UV spectra were recorded on a Beckman DU-420 spectrophotometer. $^1$H NMR spectra were recorded on a Bruker AM-600, Bruker AM-250 and Varian Gemini-200 (at 600, 250, and 200 MHz, respectively) spectrometers. 2D and $^{13}$C NMR spectra were recorded on a Bruker AC-250 spectrometer (at 62.9 and 250 MHz) in the indicated solvent using TMS as internal standard. Chemical shifts are expressed in ppm (δ) values and coupling constants (J) in Hz. Mass spectra were taken on a Finnigan-MAT 8230 spectrometer. The mention of specific instruments, instrument settings, and chromatographic media are for the purposes of example and not intended to be limiting.

EXAMPLE 2

Synthesis of Estrone to Quinol Using the Fenton Reaction Model

10β-Hydroxyestra-1,4-diene-3,17-dione (estrone-quinol) may also be synthesized from estrone using the Fenton Reaction model. As understood by those skilled in the art, in the Fenton reaction, the rate to yield the hydroxylated products of estrone, including a 10β-hydroxyestra-1,4-diene-3,17-dione quinol of the subject invention, may be influenced by several parameters including concentrations of the substrate, Fe(II) and H$_2$O$_2$, and the pH of the medium. One mL pH 3.0 sulfuric acid solution containing 300 μM Fe(II), 1.3 mM $H_2O_2$, and 100 μM estrone were incubated at 37° C. for 10 minutes, and then extracted with dichloromethane.

To assess the reaction products of estrone under the above-applied conditions, HPLC and LC/MS analyses, including MS/MS and MS/MS/MS ($MS^3$) product-ion spectra, were conducted. The extracted organic layer was washed free of acid with distilled water, dried over $Na_2SO_4$, and the solvent is evaporated under nitrogen stream. LC separation was performed using 5 cm×2.1 mm i.d. Discovery HS C-18 (SUPELCO) reversed-phase column with 0.25 mL/min water:methanol:2-propanol:acetic acid:dichloromethane (53:35:5:5:2, v/v) as a mobile phase. The sample residue removed for analysis was dissolved in 1 mL mobile phase, and 5 μL of the solution was injected for analysis. Mass spectra were recorded by a quadruple ion-trap instrument (LCQ, Finnigan MAT) using positive-ion APCI and data dependent acquisition mode to record full-scan mass spectra, MS/MS and $MS^3$ product-ion scans after collision-induced dissociation (CID) with helium as the target gas.

Figure 2A:
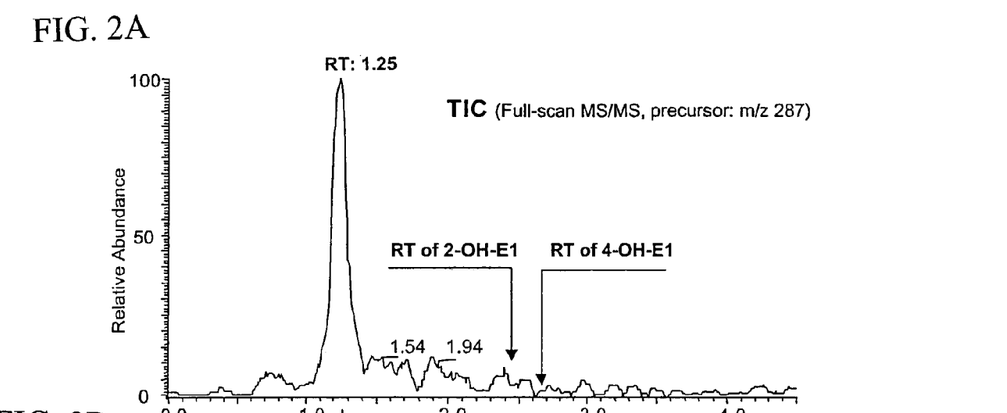
FIGS. 2A, 2B, and 2C illustrate LC/APCI-MS, MS/MS, and $MS^3$ analyses demonstrating 10β-hydroxyestra-1,4-dien-3,17-dione (estrone-quinol) as the Fenton Reaction product from estrone.
Figure 2B:
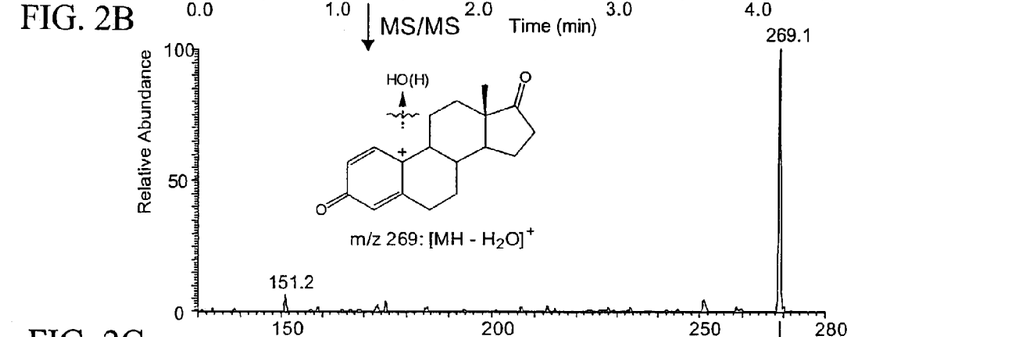
Figure 2C:
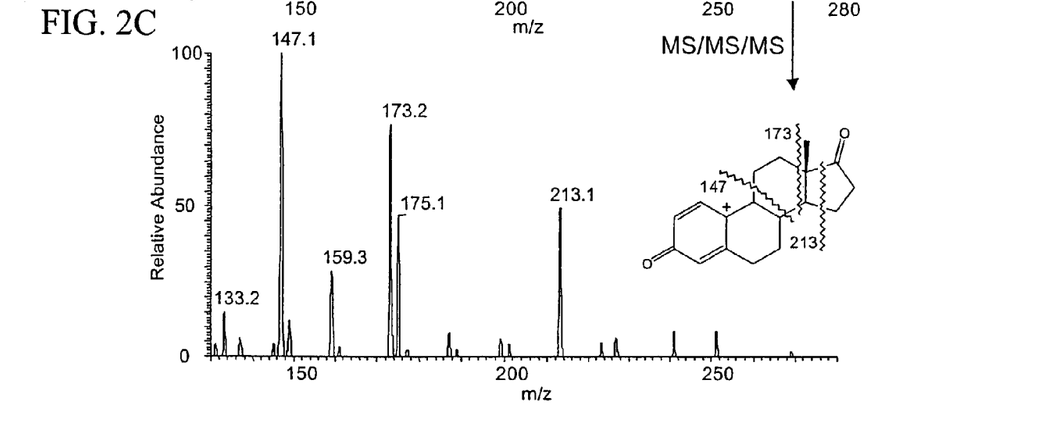

While no cathecol estrones (2-OH-E1 and 4-OH-E1) could be detected, HPLC, LC/MS analyses, and MS/MS and $MS^3$ product-ion spectra revealed that estrone-quinol was the principal reaction product, as shown in FIGS. 2A, 2B, and 2C. In particular, coelution of the results for the selected-ion monitoring (SIM; m/z 287 extracted from the successfully recorded full-scan mass spectra), the full APCI mass spectrum for the chromatographic peak (retention time ($t_R$)=1.3 minutes), the MS/MS product ion scan (peak with m/z 287 isolated as the precursor ion), and the $MS^3$ product ion scan (peak with m/z 269) with a synthetic reference compound of estrone-quinol unequivocally demonstrated the reaction product to be 10β-hydroxyestra-1,4-diene-3,17-dione (estrone-quinol).

Kinetic studies further demonstrated that oxidation of estrone to estrone-quinol proceeded rapidly under the above applied conditions. The kinetic studies revealed that that the second-order rate constant (k) of the reaction was about 20 $M^{-1}s^{-1}$ and the half-life of estrone and the initial velocity to be roughly 2.5 minutes and 1 μM/s, respectively. Further study of the Fenton reaction products formed from estrone verified that the estrone-quinol product did not undergo further oxidation (i.e., to an epoxide) and that the detectable catechol estrones remained relatively stable under Fenton conditions.

EXAMPLE 3

Synthesis of Alkylated 17β—OH of Estrogen-Related Steroidal Quinols

To alkylate the 17-OH group of the subject steroidal quinols, a steroidal quinol is initially synthesized using either the "one-pot" phenol-to-quinol transformation or the Fenton Reaction Model. The 3—OH of the resulting steroidal quinol compound is protected as benzyl (Bz) ether. The 17—OH group of the 3-benzyl steroidal quinol compound is alkylated with an alkyl halide in the presence of sodium hydride in N,N-dimethylformamide (DMF). The subsequent removal of the 3-benzyl protecting group may be performed using methods known to the skilled artisan. For example, the 3-benzyl protecting group may be removed using a Parr hydrogenator with Palladium on charcoal (Pd/C) as the catalyst in glacial acetic acid.

EXAMPLE 4

Figure 3:
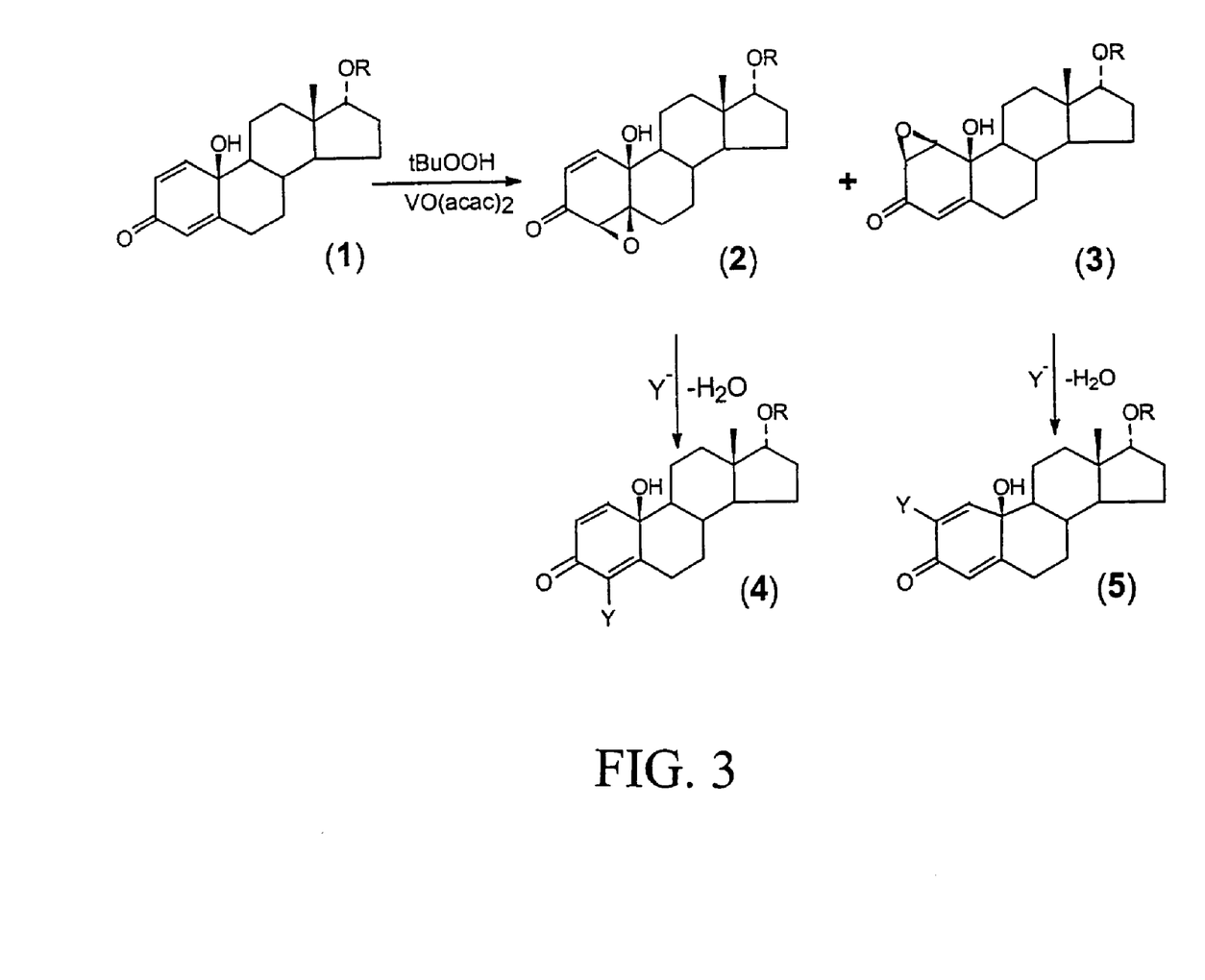
FIG. 3 illustrates preparatory schemes for the synthesis of 4-substituted or 2-substituted prodrug forms of compounds of the present invention.

Synthesis of 2-substituted or 4-substituted Estrogen-Related Steroidal Quinols FIG. 3 illustrates the synthesis of 4-substituted or 2-substituted estrogen related quinols according to the subject invention. As with the estrone quinol, the first step in synthesizing 2-subsituted or 4-substituted estrogen-related steroidal quinol compounds includes a "one-pot" phenol-to-quinol transformation. By way of example, the initial step in synthesizing 10β-hydroxy-4β,5β-epoxyestr-1-ene-3,17-dione includes stirring a solution of estrone, m-CPBA, and $(BzO)_2$ in a mixture of $CH_2Cl_2/Me_2CO$ (4/1) which is heated to reflux for 24 hours while irradiated with 60 W tungsten lamp (not shown). The resulting estrogen-related steroidal quinol compound is then subjected to a lipid hydroperoxide model compound such as tert-butyl hydroperoxide (tBuOOH) and vanadyl acetylacetonate [$VO(acac)_2$]. A nucleophile (e.g. sodium bromide or lithium methylate) of either the 2- or 4- substituent is added to the resulting epoxide compounds. The addition of a nucleophile results in the spontaneous removal of $H_2O$ to provide a 2-substituted or 4-substituted steroidal quinol according to the present invention.

EXAMPLE 5

Synthesis of 2,4-disubstituted Estrogen-Related Steroidal Quinols

Figure 4:
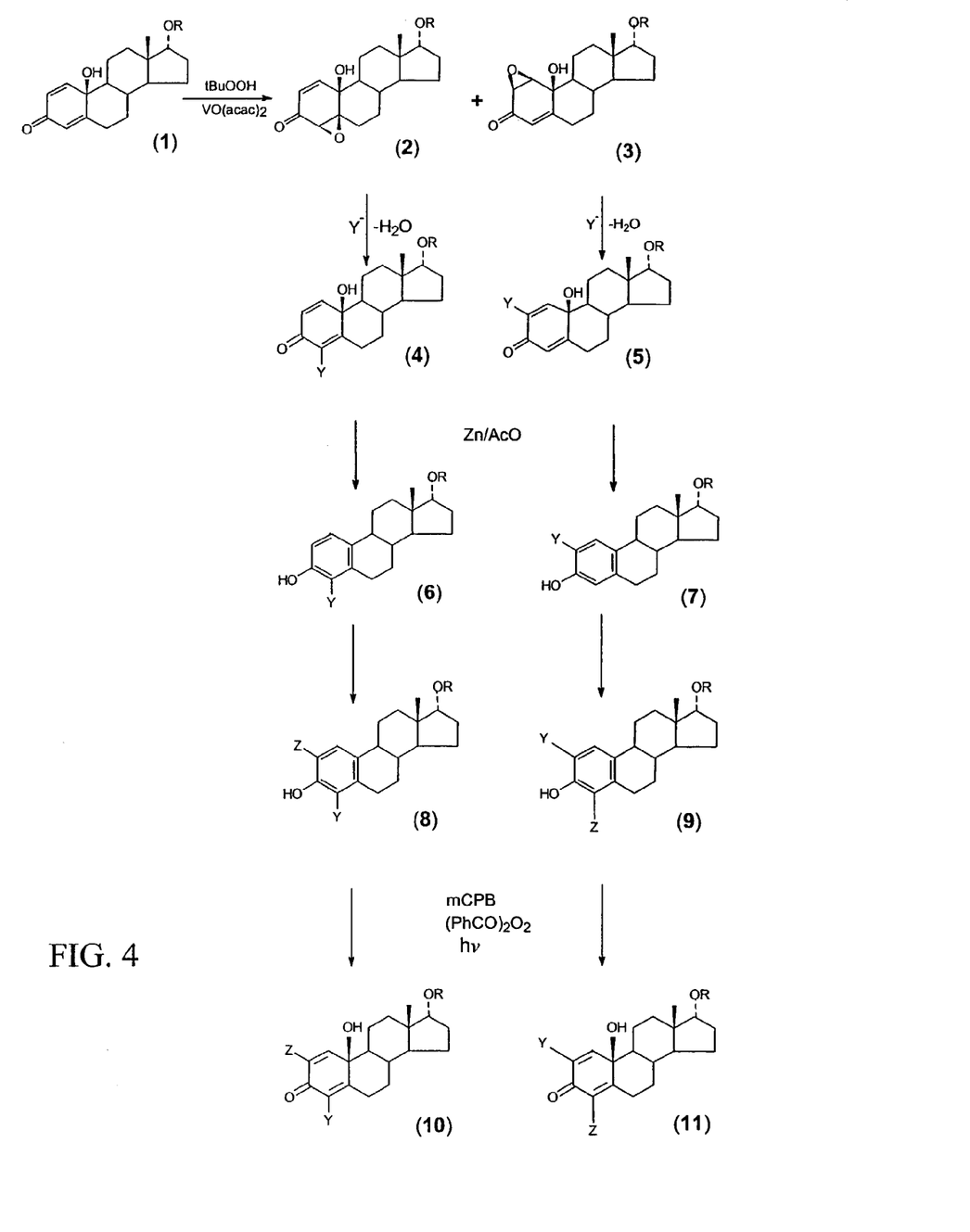
FIG. 4 illustrates preparatory schemes for the synthesis of 2,4-disubstituted prodrug forms of compounds of the present invention.

Synthesis of 2,4-disubstituted estrogen-related steroidal quinols is illustrated in FIG. 4. As with the synthesis of the 2-substituted or 4-substituted, the first step in synthesizing a 2,4-substituted estrogen-related steroidal quinol compounds includes a "one-pot" phenol-to-quinol transformation. The estrogen-related steroidal quinol is then subjected to a lipid hydroperoxide model compound such as tert-butyl hydroperoxide (tBuOOH) and vanadyl acetylacetonate [$VO(acac)_2$]. To the resulting epoxide compounds, a nucleophile (e.g. sodium bromide or lithium methylate) is introduced to provide a 2- or 4- substituent. The addition of a nucleophile results in the spontaneous removal of $H_2O$ to provide a 2-substituted or 4-substituted steroidal quinol according to the present invention. The resulting 2-substituted or 4-substituted steroidal quinol is then subjected to zinc in acetic acid to make the compounds phenolic. The phenolic compounds are then subjected to a "one-pot" phenol-to-quinol transformation. By way of analogy, the phenolic 2-substiuted or 4-substituted estrogen-related steroidal compound is subjected to a lipid hydroperoxide model compound such as tert-butyl hydroperoxide (tBuOOH) and vanadyl acetylacetonate [$VO(acac)_2$]. To the resulting epoxide compounds, a nucleophile (e.g. sodium bromide or lithium methylate) is introduced to provide a 2- or 4- substituent. The addition of a nucleophile results in the spontaneous removal of $H_2O$ to provide a phenolic 2,4-disubstituted steroidal compound. The 2,4-disubstituted steroidal compound is then stirred with m-CPBA and $(PhCO)_2O_2$ in $CCl_4/Me_2CO$ to reflux while irradiated with a 60 Watt tungsten lamp to provide a 2,4-disubstituted steroidal quinol according to the present invention.

EXAMPLE 6

Synthesis of 1,2,4-trisubstituted Estrogen-Related Steroidal Quinols

Figure 5:
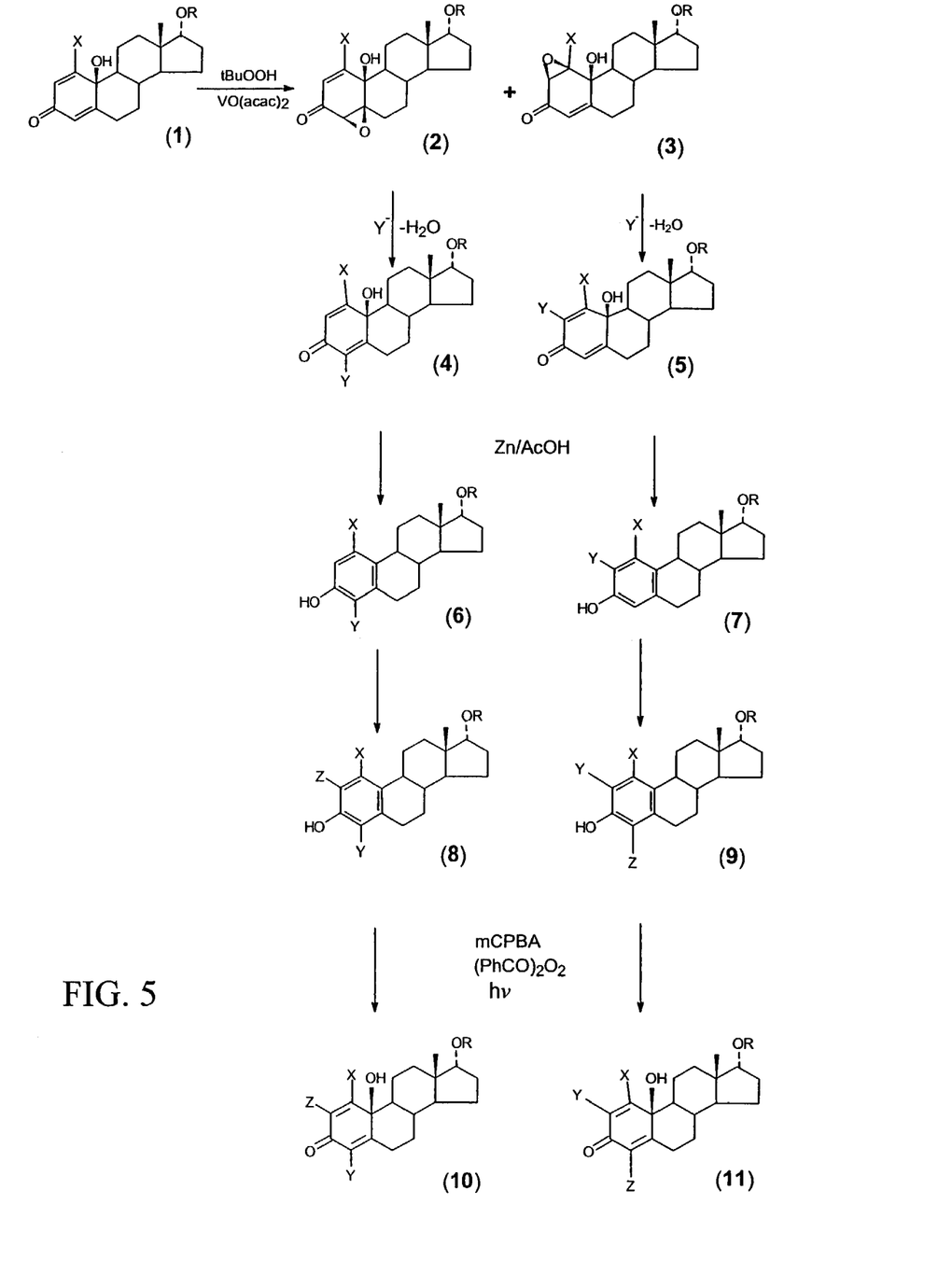
FIG. 5 illustrates preparatory schemes for the synthesis of 1,2,4-trisubstituted prodrug forms of compounds of the present invention.

Synthesis of 1,2,4-trisubstituted steroidal quinols is illustrated in FIG. 5. As with the synthesis of the 2,4-substituted, the first step in synthesizing a 2,4-substituted estrogen-related steroidal quinol compounds includes a "one-pot" phenol-to-quinol transformation of a 1-substituted estrogen compound. The resulting 1-substituted estrogen-related steroidal quinol is then subjected to a lipid hydroperoxide model compound such as tert-butyl hydroperoxide (tBuOOH) and vanadyl acetylacetonate [VO(acac)$_2$]. To the resulting epoxide compounds, a nucleophile (e.g. sodium bromide or lithium methylate) is introduced to provide a 2- or 4- substituent. The addition of a nucleophile results in the spontaneous removal of H$_2$O to provide a 1,2-disubstituted or 1,4-substituted steroidal quinol according to the present invention. The resulting 1,2-disubstituted or 1,4-disubstituted steroidal quinol is then subjected to zinc in acetic acid to make the compounds phenolic. The phenolic compounds are then subjected to a "one-pot" phenol-to-quinol transformation. By way of analogy, the phenolic 1,2-disubstiuted or 1,4-disubstituted estrogen compound is subjected to a lipid hydroperoxide model compound such as tert-butyl hydroperoxide (tBuOOH) and vanadyl acetylacetonate [VO(acac)$_2$]. To the resulting epoxide compounds, a nucleophile (e.g. sodium bromide or lithium methylate) is introduced to provide a 2- or 4- substituent. The addition of a nucleophile results in the spontaneous removal of H$_2$O to provide a phenolic 1,2,4-trisubstituted steroidal compound. The 1,2,4-trisubstituted steroidal compound is then stirred with m-CPBA and (PhCO)$_2$O in CCl$_4$/Me$_2$CO to reflux while irradiated with a 60 Watt tungsten lamp to provide a 1,2,4-trisubstituted steroidal quinol according to the present invention.

Numerous other quinols for phenolic estrogens or estrogen analogs according to the present invention, as well as related, equivalent compounds, may be readily synthesized by analogy by simply modifying the above-described synthetic pathways, utilizing methods that are known to those of ordinary skill in the art.

The following Examples 7–9 describe experiments demonstrating the ability of the compounds of the present invention to be reduced into an active steroidal phenol structure and regenerated by capturing hydroxyl radicals.

EXAMPLE 7

Figure 6:
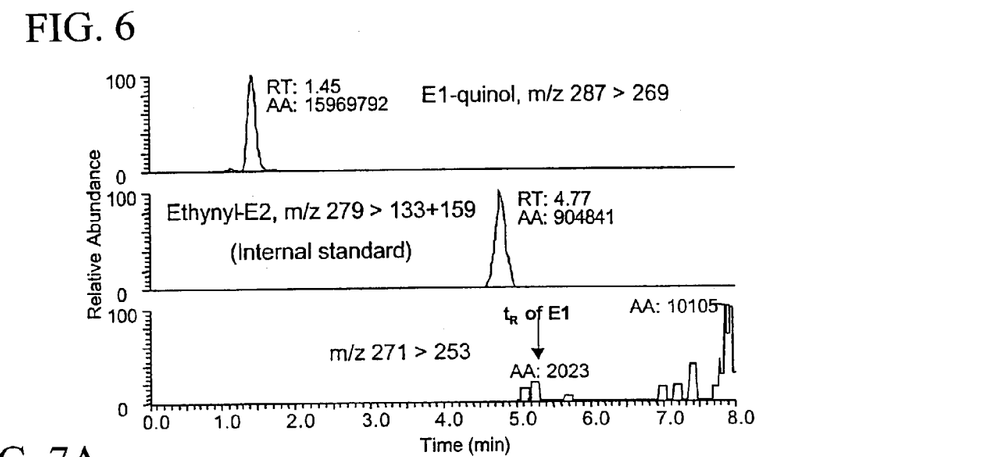
FIG. 6 illustrates chromatographic traces for the analytes, estrone-quinol and estrone, and the internal standard (ethynyl-estradiol) in the control experiment.
Figure 7A:
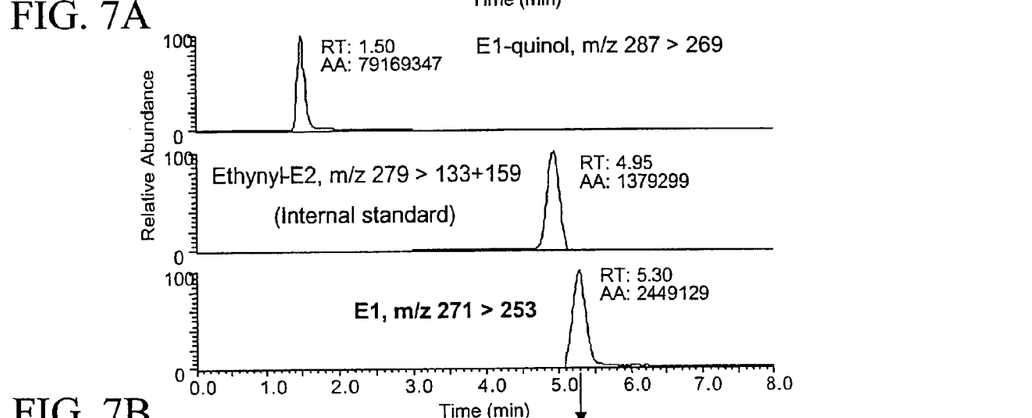
FIGS. 7A and 7B illustrate the chromatographic traces for the analytes, estrone-quinol and estrone, and the internal standard (ethynyl-estradiol) in NADPH, and LC/APCI-MS/MS analyses demonstrating the reduction of estrone-quinol to estrone by NADPH, respectively.
Figure 7B:
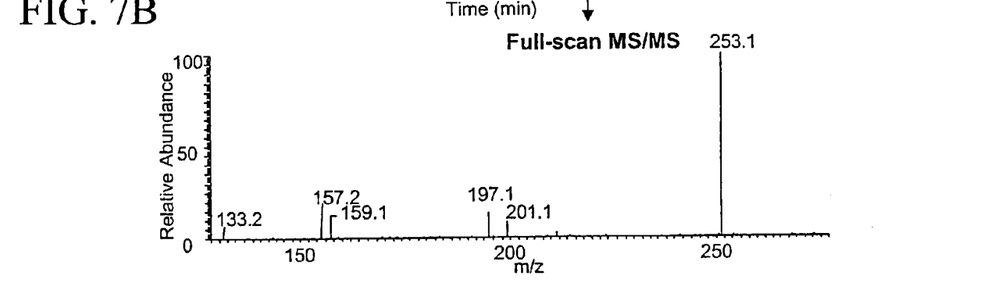

In vitro Study Demonstrating the Reduction of Estrogen-Related Steroidal Quinol into an Active Structure Estrone-quinol (0.1 mM) was incubated at 37° C. in 0.1 M phosphate buffer pH 7.5 in the presence of 1 mM of NADH, NADPH, sodium ascorbate, and glutathione (GSH). Aliquots (500 µl) were taken after 60 minutes of incubation, and extracted with ethyl acetate. After removing the solvent, the residue of the combined organic extracts was analyzed for their estrone content by LC/MS/MS using ethynyl-estradiol as an internal standard. Control incubations (0.1 mM estrone-quinol in 0.1 M phosphate buffer at pH 7.5 and 37° C. without the addition of a reducing agent were performed, as shown in FIG. 6, as well as incubation with GSH found to be free of estrone even after 12 hours. Trace amounts of estrone could be detected when the incubation was carried out in the presence of NADH and, especially, NADPH, as shown in FIGS. 7A and 7B.

EXAMPLE 8

In vitro Reduction of an Estrogen-Related Steroidal Quinol into an Active Steroidal Phenol Structure Estrone-quinol (100 µM, 286 µg/mL) was incubated at 37° C. in 0.1 M phosphate buffer (pH 7.5) in the presence of NADPH (1 mM) and male rat liver microsomes (1 mg/ml final protein concentration). Aliquots (500 µl) were taken after 5 minutes of incubation with rat liver microsomes. Estrone quinol was found to undergo reduction to form estrone. In addition, the concentration of estrone reached after 5 minutes of microsomal incubation was about 12-times higher (15.1 µg/mL) than the value of 1.2 µg/mL measured without the addition of the microsomes in the relevant control experiment (NADPH present but microsomes not added.

EXAMPLE 9

In vivo Experiment Demonstrating the Reduction of an Estrogen-Related Steroidal Quinol into an Active Phenol Steroidal Structure Cerebral microdialysis experiments were performed to establish that estrone-quinol undergoes reduction to estrone in neuronal cells in vivo.

Male, Sprague rats (300–400 g) were anesthetized, placed in a stereotaxic instrument, and a guide cannula (CMA/12 guide cannula) was implanted into the ventral hippocampus under aseptic conditions. The guide cannula was fixed to the skull, together with stainless steel screws attached into additional two holes, with dental acrylics. Before starting the experiment (usually 5–7 days after the implantation of the guide cannula implantation) the rats were placed in a containment unit (BAS, Inc.) for at least 30 minutes. Then a microdialysis probe (CMA/12 polycarbonate membrane diameter 0.5 mm; membrane length 4 mm; molecular cut off: 5,000 Da) was inserted into the ventral hippocampus through the guide cannula. After insertion, the microdialysis probe was perfused with an artificial cerebrospinal fluid (aCSF) at a flow rate of 1 µl/min. maintained by a microperfusion pump (BAS BeeStinger) attached to the probe via polyethylene tubing and a liquid swivel. After equilibration for 50 minutes, an automatic refrigerated fraction collector (BAS HoneyComb) was used for continuous sampling of the probe efflux for 24 hours in 60 minute fractions collected into 300-µl glass vials (control). The artificial cerebrospinal fluid was then replaced by a perfusion solution containing 10 picomole/µL of estrone-quinol in aCSF (By measuring the, decrease in the concentration of compound from the perfused solution, estrone-quinol entered the brain with a flux of about 2 picomole/minute). The sample collection was continued for another 24 hours. For LC/APCI-MS/MS analysis, 50 µl each from 20 fractions (1 mL total volume) of the control and the estrone-quinol microdialysis experiments, respectively, were combined and extracted with ethyl acetate after the addition of the internal standard.

Figures 8A, 8B:
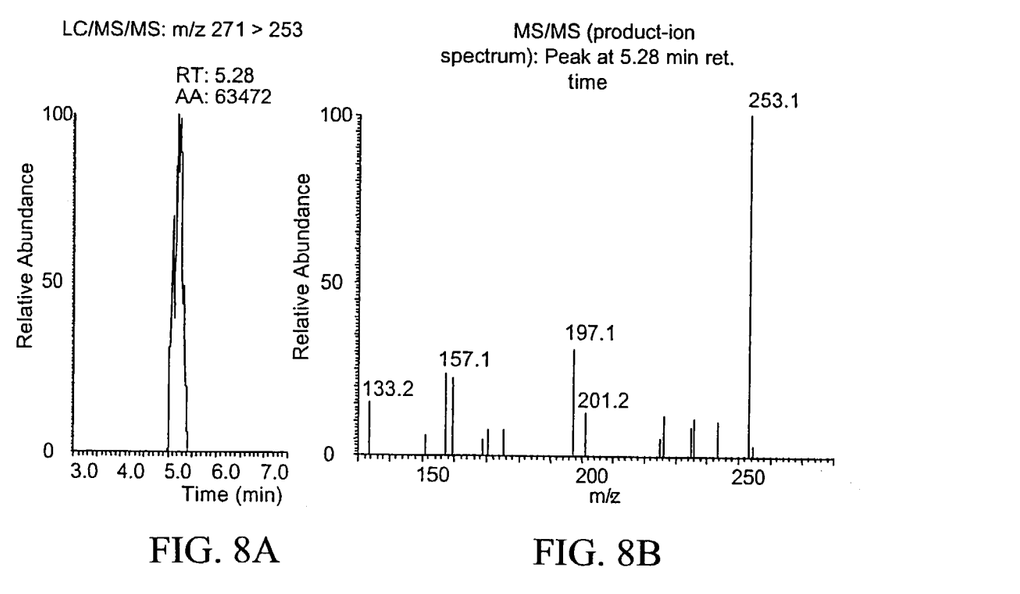
FIGS. 8A and 8B illustrate the LC/APCI-MS/MS analysis of the ethyl acetate extract from the in vivo cerebral microdialysate obtained after probe perfusion at 1 μL/minute with 10-picomole/μL of estrone-quinol artificial cerebrospinal fluid.

Although estrone was not detectable in the control microdialysates, it was present in a detectable quantity in samples collected during the perfusion of the probes with the aCSF-solution containing estrone-quinol, as shown in FIGS. 8A and 8B. The chromatographic traces displayed the SRM m/z 287→m/z 269 SRM for estrone-quinol and m/z 271 m/z 253 for estrone. The peak at $t_R$=4.5 minutes was unequivocally identified, based on coelution with an authentic reference compound and identical APCI, MS/MS (given together with the origin of the major fragments observed) and $MS^3$ spectra, as estrone.

The following Examples 10 and 11 describe experiments that demonstrate equivalence in the bioactivity and effectiveness of the quinols of the present invention as compared to the phenolic estrogen compound.

EXAMPLE 10

In vitro Neural Cell Viability after Exposure to Oxidative Stress and Treatment with a Steroidal Quinol of the Present Invention Compared with that of the Active Phenolic Structure HT-22 cells were cultured in Dulbecco's Modified Eagle's media supplemented with 10% fetal bovine serum. Experiments were performed in 96-well culture plates containing approximately 5,000 cells/well as determined by a Neubauer hemacytometer. The cells were incubated for 24 hours. 10β-hydroxy-17β-butoxyestra-1,4-diene-3-one and the phenolic steroidal parent structure 3-hydroxy-17β-butoxyestra-1,3,5-triene were each dissolved in absolute ethanol and diluted with the culture medium, and the plate incubated for 24 hours after sodium glutamate (20 mM) was added. Cell viability was quantified by the Calcein AM assay in a phosphate buffer solution.

Figure 9:
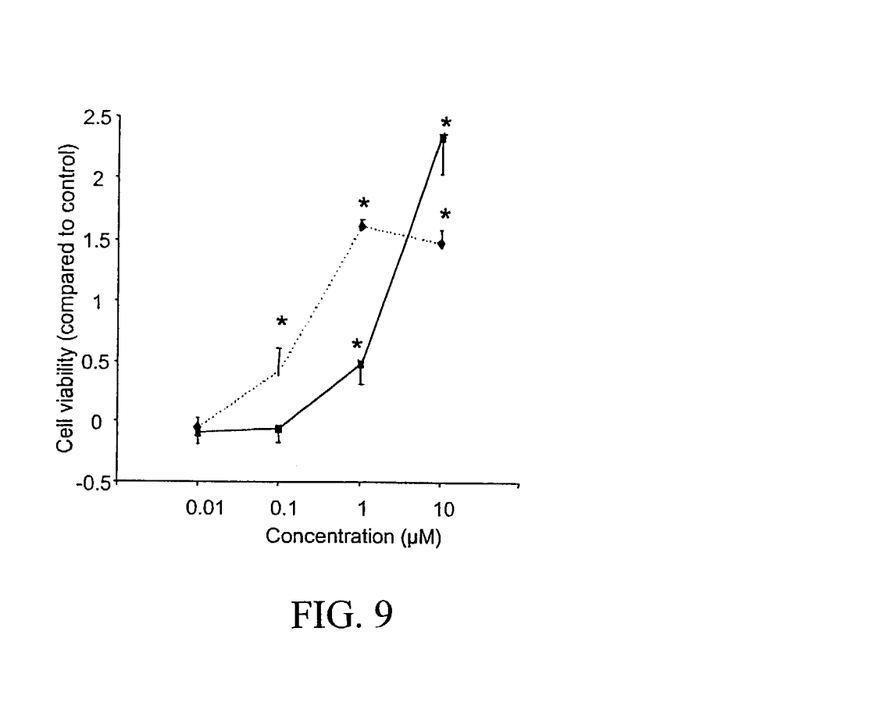
FIG. 9 illustrates cell viability after exposure to glutamate-induced oxidative stress and treatment with an embodiment of the present invention as compared to the active phenolic parent compound.

At 1 μM and 10 μM concentrations of 10β-hydroxy-17β-butoxyestra-1,4-diene-3-one, there was demonstrable neuroprotective activity against glutamate-induced oxidative stress in HT22 neuronal cells, as shown in FIG. 9. Although the 10β-hydroxy-17β-butoxyestra-1, 4-diene-3-one compound does not have a phenolic A-ring considered an essential component for the radical scavenging activity, the structural requirement for the radical scavenging activity, such as a phenolic moiety, is provided via a reductive activation. In essence, the quinol 10β-hydroxy-17β-butoxyestra-1,4-diene-3-one of the present invention serves as a prodrug for the active steroidal structure 3-hydroxy-17β-butoxyestra-1, 3,5-triene.

EXAMPLE 11

In vivo Neural Cell Protection Against Stroke and Treatment with a Steroidal Quinol of the Present Invention Compared with that of the Active Phenolic Structure Acute restoration of blood flow after ischemia leads to the production of ROS (Forman, L. G. et al., "Augmentation of nitric oxide, superoxide, and peroxynitrite production during cerebral ischemia and reperfusion in the rat," *Neurochem. Res.*, 23:141–148 (1998); Peters, O. et al., "Increased formation of reactive oxygen species after permanent and reversible middle cerebral artery occlusion in the rat," *J. Cereb. Blood Flow Metab.*, 18:196–205 (1998); and Mason, R. B. et al., "Production of reactive oxygen species after reperfusion in vitro and in vivo: protective effect of nitric oxide," *J. Neurosurg.*, 93:99–107 (2000)) that are directly toxic to neurons. Therapeutic, non-enzymatic scavenging of free radicals can be a viable strategy for the reduction of ischemic cerebral tissue damage.

Female Sprague-Dawley rats (weighing 200–250 g, Charles River, Wilmington, Mass.) were acclimatized for three days prior to surgery. Bilateral ovariectomy was performed 2 weeks before middle cerebral artery occlusion (MCAO). Animals were anesthetized by intraperitoneal injection of ketamine (60 mg/kg) and xylazine (10 mg/kg). Rectal temperature was maintained at 37.5±0.5° C. during the procedure. The middle cerebral artery was occluded for one hour and then suture was withdrawn for reperfusion. Estrone and a quinol of the present invention (E1-quinol) were dissolved in corn oil and administered at a dose of 200 μg/kg subcutaneously (sc) 2 h prior to the onset of the 1-h MCAO.

Animals were decapitated 24 hours after reperfusion. Brains were harvested and placed in a brain matrix for slicing (Harvard Apparatus, Holliston, Mass.). Seven slices were made at 3, 5, 7, 9, 11, 13 and 15 mm posterior to the olfactory bulb. Slices were incubated for 30 minutes in 2% solution of 2,3,5-triphenyltetrazolium chloride at 37° C., and then fixed in 10% formalin. The stained slices were photographed and subsequently measured for the ischemic lesion volume (Image-Pro Plus 4.1, Media Cybernetics, Silver Spring, Md.).

Figure 10:
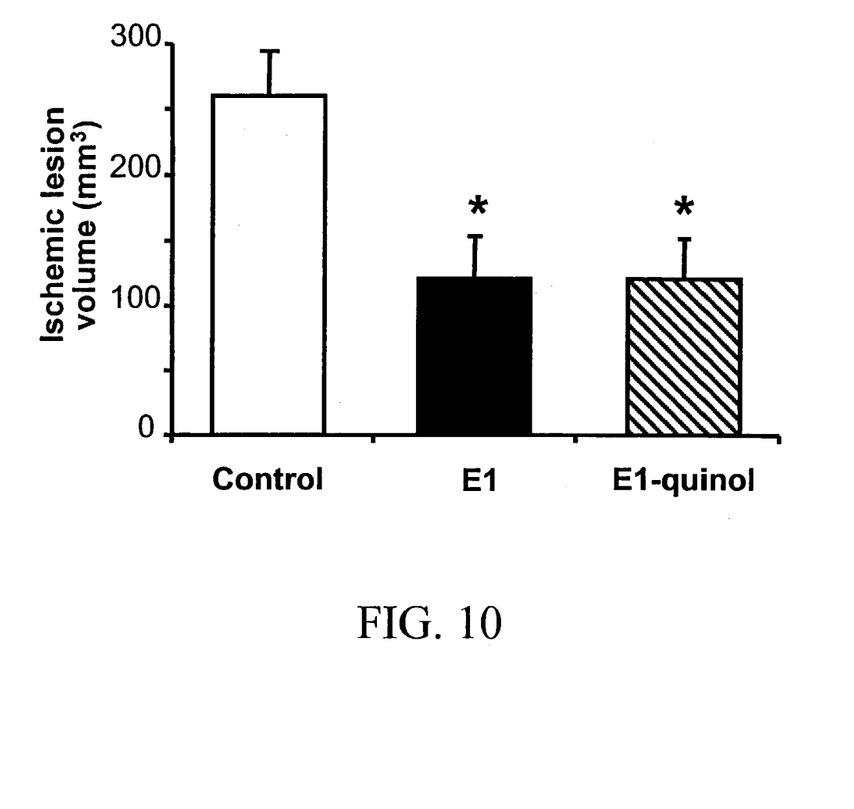
FIG. 10 illustrates the effect of a quinol of the subject invention on reperfusion-associated ischemic damage.

When administered before ischemia, the estrogen (estrone) significantly reduced infarct volume by 53% ($P<0.05$) compared to control after transient MCAO followed by 24-h reperfusion in ovariectomized rats. Further, the E1-quinol of the present invention was equipotent with the parent estrogen (estrone) in reducing lesion, as illustrated in FIG. 10. The data in FIG. 10 are expressed as mean ±SEM. Statistical evaluations were done by one-way ANOVA followed by post hoc Dunnett's (comparison to a single control group) or Student-Newman-Keuls test (multiple comparisons).

This Example and previous studies demonstrate that natural estrogens employed at supraphysiological concentrations (Yang, S. H. et al., "Estradiol exerts neuroprotective effects when administered after ischemic insult," *Stroke*, 31:745–749 (2000) and Shi, J. et al., Estrogens decrease reperfusion-associated cortical ischemic damage: an MRI analysis in a transient focal ischemia model,"*Stroke*, 32:987–992 (2001)) and estrogen analogues with no affinity to estrogen receptors (Liu, R. et al., "Neuroprotective effects of a novel non-receptor-binding estrogen analogue: in vitro and in vivo analysis," *Stroke*, 33:2485 –2491 (2002)) are neuroprotective. Thus, the observed effect of both the estrone and the E1-quinol of the present invention can be due in part to an antioxidant mechanism in this Example. The E1-quinol of the present invention showed a decrease of reperfusion-associated ischemic damage equivalent to that of the parent estrogen (estrone) in the in vivo paradigm, which indicates the conversion of the quinol to the neuroprotective, biologically active phenolic A-ring estrogen compound. Further, the quinols of the present invention are pharmaceutically more acceptable (i.e. as prodrugs) due to their ability in vivo to be less lipophilic, more resistant to oxidative metabolism, safer/less toxic, and less likely to cause an unwanted hormonal effect than the parent phenolic/estrogen compounds.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A method of providing biologically active estrogen compounds to a mammal, wherein said method comprises administering to the mammal an effective amount of a quinol that is convened to a biologically active estrogen compound via enzyme-catalyzed reduction, wherein the quinol has the general structure:

wherein
- R is selected from the group consisting of H, alkyl, cycloalkyl, aryl, heterocycle, heteroaryl, alkylamino, hydroxyalkyl, alkoxyalkyl, and alkylaryl;
- X is selected from the group consisting of hydrogen, halogen, isopropyl, alkyl, alkenyl, alkynyl, carbocycle, cycloalkyl, aryl, heterocycle, heteroaryl, alkylamino, hydroxyalkyl, alkoxyalkyl, and a linear or branched hydrocarbon from 1–15 carbon atoms in length, that can optionally include one or more heteroatoms in the chain;
- Y is selected from the group consisting of hydrogen, halogen, isopropyl, alkyl, alkenyl, alkynyl, carbocycle, cycloalkyl, aryl, heterocycle, heteroaryl, alkylamino, hydroxyalkyl, alkoxyalkyl, and a linear or branched hydrocarbon from 1–15 carbon atoms in length, that can optionally include one or more heteroatoms in the chain; and
- Z is selected from the group consisting of hydrogen, halogen, isopropyl, alkyl, alkenyl, alkynyl, carbocycle, cycloalkyl, aryl, heterocycle, heteroaryl, alkylamino, hydroxyalkyl, alkoxyalkyl, and a linear or branched hydrocarbon from 1–15 carbon atoms in length, that can optionally include one or more heteroatoms in the chain.

2. The method according to claim 1, wherein R is a butyl group and X, Y, and Z are hydrogen.

3. The method according to claim 1, wherein X and Y are hydrogen, and Z is not hydrogen.

4. The method according to claim 1, wherein X and Z are hydrogen, and Y is not hydrogen.

5. The method according to claim 1, wherein X is hydrogen.

6. The method according to claim 1, further comprising administering the quinol by a route selected from the group consisting of oral, buccal, intramuscular, transdermal, intravenous, and subcutaneous.

7. A quinol that is converted to a biologically active estrogen compound via enzyme catalyzed reduction and having the general structure wherein R is a butyl group and X, Y, and Z are hydrogen.

8. A pharmaceutical composition comprising a quinol that is converted to a biologically active estrogen compound via enzyme catalyzed reduction, wherein said composition further comprises a pharmaceutically acceptable carrier, wherein the quinol has the general structure:

wherein R is a butyl group and X, Y, and Z are hydrogen.

* * * * *

UNITED STATES PATENT AND TRADEMARK OFFICE
CERTIFICATE OF CORRECTION

| | |
|---|---|
| PATENT NO. | : 7,026,306 B2 |
| APPLICATION NO. | : 10/405413 |
| DATED | : April 11, 2006 |
| INVENTOR(S) | : Laszlo Prokai, Katalin Prokai and James Simpkins |

It is certified that error appears in the above-identified patent and that said Letters Patent is hereby corrected as shown below:

Column 8,
Line 23, "osteomyclitis" should read --osteomyelitis--.
Line 29, "dernatitis" should read --dermatitis--.

Column 17,
Claim 1, line 5, "convened" should read --converted--.

Signed and Sealed this

Eleventh Day of July, 2006

JON W. DUDAS
*Director of the United States Patent and Trademark Office*